(12) United States Patent
Christakis et al.

(10) Patent No.: US 10,835,401 B2
(45) Date of Patent: Nov. 17, 2020

(54) HYDRATION DELIVERY SYSTEM FOR STENTS

(71) Applicant: BOSTON SCIENTIFIC SCIMED, INC., Maple Grove, MN (US)

(72) Inventors: Laura E. Christakis, Boston, MA (US); Colby Harris, Weston, MA (US); Gerald Fredrickson, Westford, MA (US); Ramon Libarnes, Fort Madison, IA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 115 days.

(21) Appl. No.: 15/852,716

(22) Filed: Dec. 22, 2017

(65) Prior Publication Data

US 2018/0185184 A1 Jul. 5, 2018

Related U.S. Application Data

(60) Provisional application No. 62/440,245, filed on Dec. 29, 2016.

(51) Int. Cl.
*A61F 2/95* (2013.01)
*A61F 2/962* (2013.01)
*A61F 2/966* (2013.01)

(52) U.S. Cl.
CPC .............. *A61F 2/95* (2013.01); *A61F 2/962* (2013.01); *A61F 2/966* (2013.01)

(58) Field of Classification Search
CPC .... A61F 2/95; A61F 2/958; A61F 2002/9505; A61F 2002/95823; A61F 2002/9583; A61F 2002/9586; A61F 2002/826; A61F 2/966; A61M 25/10
See application file for complete search history.

(56) References Cited

U.S. PATENT DOCUMENTS

| | | | | |
|---|---|---|---|---|
| 4,762,128 A | * | 8/1988 | Rosenbluth | A61F 2/04 604/103.08 |
| 4,893,623 A | * | 1/1990 | Rosenbluth | A61F 2/91 604/104 |
| 5,603,698 A | * | 2/1997 | Roberts | A61F 2/95 604/104 |
| 5,632,760 A | * | 5/1997 | Sheiban | A61F 2/958 604/96.01 |

(Continued)

FOREIGN PATENT DOCUMENTS

| | | |
|---|---|---|
| WO | 9511055 A1 | 4/1995 |
| WO | 2014142808 A1 | 9/2014 |

OTHER PUBLICATIONS

International Search Report and Written Opinion dated Mar. 14, 2018 for International Application No. PCT/US2017/068215 (11 pages).

*Primary Examiner* — Dianne Dornbusch
(74) *Attorney, Agent, or Firm* — Seager, Tufte & Wickhem, LLP

(57) ABSTRACT

A stent delivery device is provided that includes an inner member defining a distal tip and a stent holding region, and an outer tubular member slidingly disposed over the inner member and configured to engage the distal tip. Seal members may be disposed on one or more of an outer surface of the inner member, the distal tip, and the outer tubular member. The seal members define a liquid-tight sealed chamber surrounding the stent holding region.

19 Claims, 17 Drawing Sheets

(56) References Cited

U.S. PATENT DOCUMENTS

| | | | |
|---|---|---|---|
| 5,817,101 A * | 10/1998 | Fiedler | A61F 2/95 623/1.11 |
| 5,961,536 A * | 10/1999 | Mickley | A61M 25/10 604/96.01 |
| 6,004,328 A | 12/1999 | Solar | |
| 6,123,712 A * | 9/2000 | Di Caprio | A61F 2/95 606/108 |
| 6,168,617 B1 | 1/2001 | Blaeser et al. | |
| 6,254,611 B1 | 7/2001 | Vrba | |
| 6,447,835 B1 | 9/2002 | Wang et al. | |
| 6,602,226 B1 * | 8/2003 | Smith | A61F 2/958 604/101.02 |
| 6,626,936 B2 | 9/2003 | Stinson | |
| 6,764,504 B2 * | 7/2004 | Wang | A61F 2/958 606/194 |
| 6,890,348 B2 | 5/2005 | Sydney et al. | |
| 7,785,361 B2 * | 8/2010 | Nikolchev | A61F 2/90 623/1.11 |
| 8,475,515 B2 * | 7/2013 | Dorn | A61F 2/95 623/1.11 |
| 9,700,701 B2 * | 7/2017 | Benjamin | A61M 25/0097 |
| 2002/0045929 A1 | 4/2002 | Diaz | |
| 2002/0120321 A1 * | 8/2002 | Gunderson | A61F 2/958 623/1.11 |
| 2003/0105508 A1 * | 6/2003 | Johnson | A61F 2/958 623/1.11 |
| 2004/0102791 A1 * | 5/2004 | Murray, III | A61F 2/958 606/108 |
| 2004/0249343 A1 * | 12/2004 | Cioanta | A61B 18/04 604/113 |
| 2006/0229700 A1 * | 10/2006 | Acosta | A61F 2/915 623/1.11 |
| 2006/0271151 A1 * | 11/2006 | McGarry | A61B 17/12045 623/1.11 |
| 2008/0119922 A1 * | 5/2008 | Alkhatib | A61F 2/958 623/1.11 |
| 2015/0057738 A1 * | 2/2015 | Hepke | A61F 2/2436 623/1.11 |

\* cited by examiner

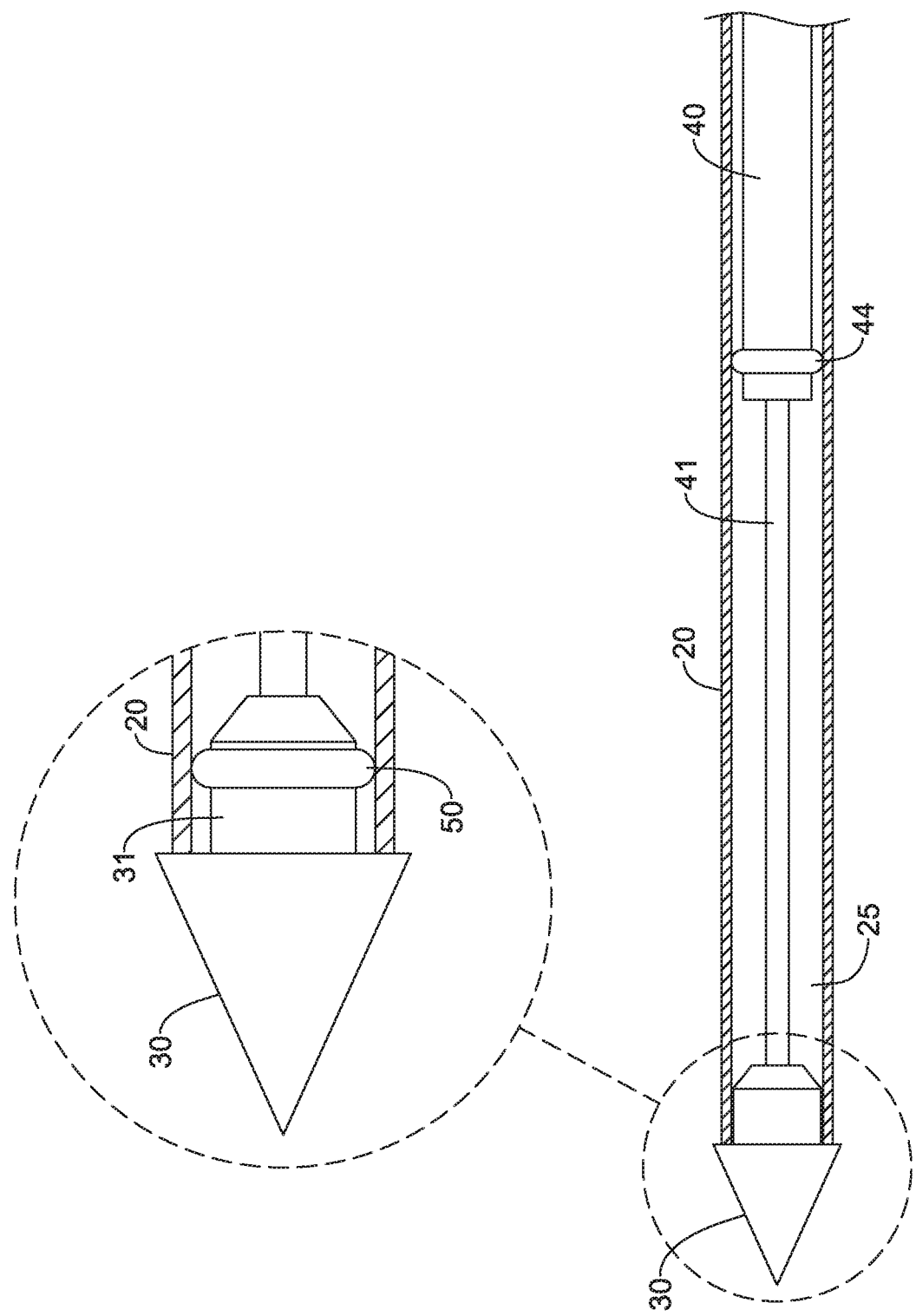

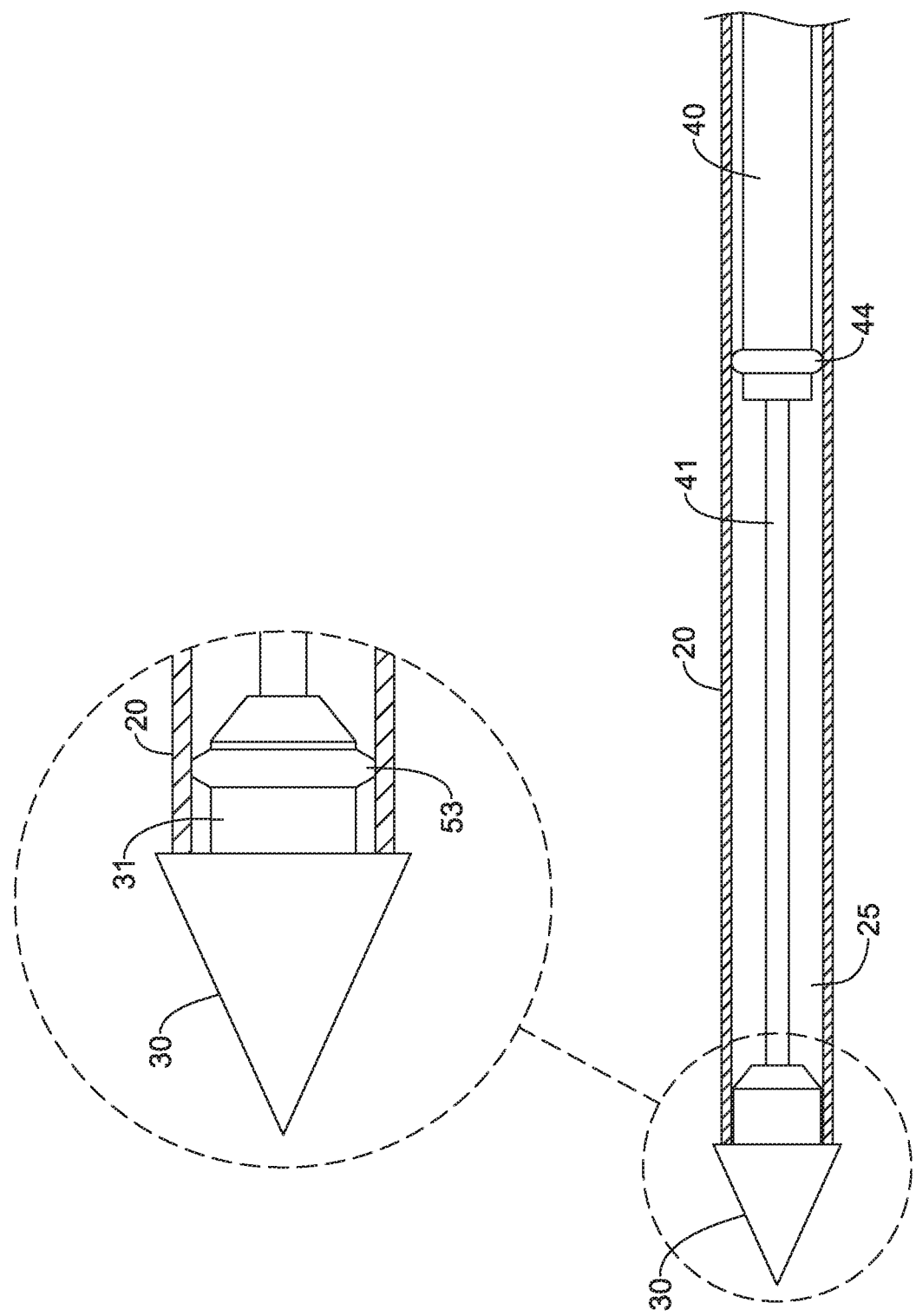

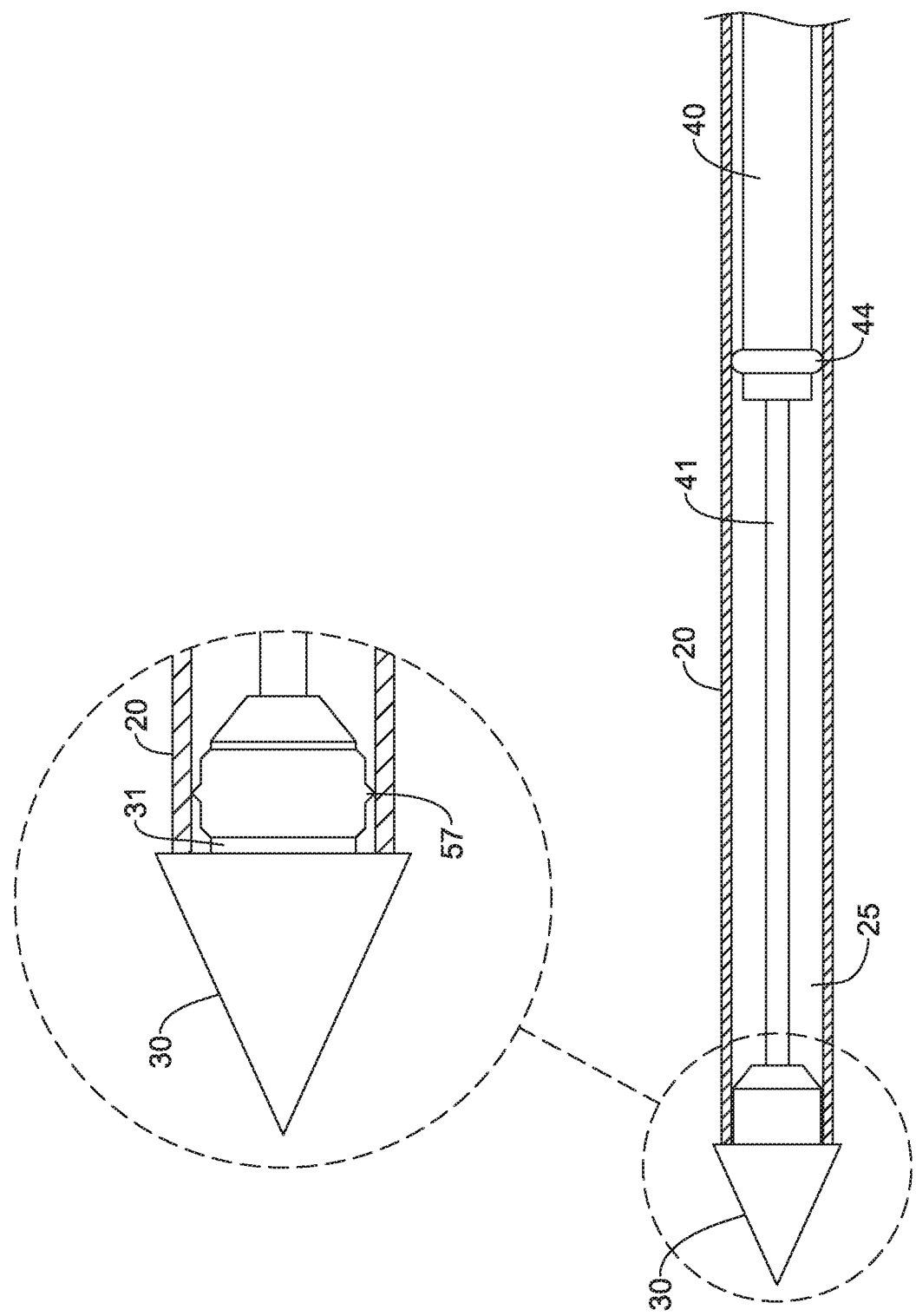

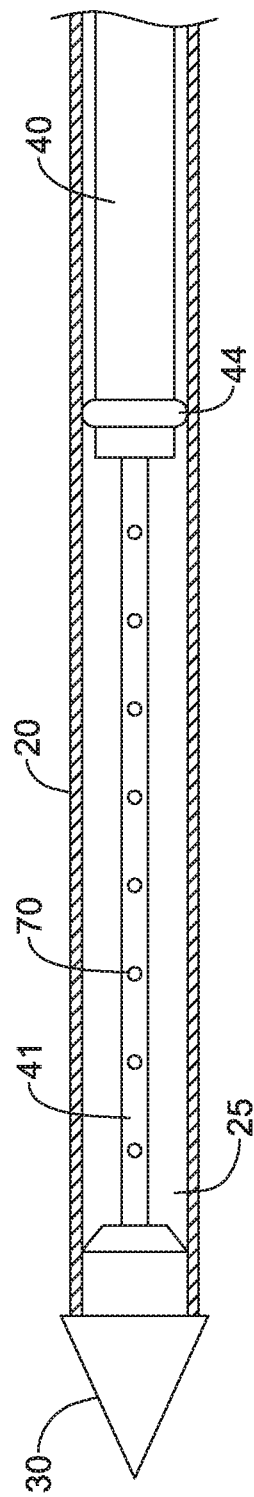

HYDRATION DELIVERY SYSTEM FOR STENTS

CROSS-REFERENCE TO RELATED APPLICATIONS

This application claims priority to U.S. Provisional Application Ser. No. 62/440,245, filed Dec. 29, 2016, the entirety of which is incorporated herein by reference.

TECHNICAL FIELD

The disclosure is directed to devices and methods for loading, transporting, and delivering stents. More particularly, the disclosure is directed to methods and systems for loading and delivering radially distensible stents in a liquid environment.

BACKGROUND

An intraluminary prosthesis is a medical device used in the treatment of diseased bodily lumens. One type of intraluminary prosthesis used in the repair and/or treatment of diseases in various body lumens is a stent. A stent is generally a longitudinal tubular device formed of biocompatible material which is useful to open and support various lumens in the body. For example, stents may be used in a bodily lumen, such as in the coronary or peripheral vasculature, esophagus, trachea, bronchi, colon, biliary tract, urinary tract, prostate, brain, as well as in a variety of other applications in the body. These devices are implanted within the body lumen to open and/or reinforce collapsing or partially occluded sections of the lumen.

Stents generally include an open flexible configuration. This configuration allows the stent to be inserted through curved body lumens. Furthermore, this configuration allows the stent to be configured in a radially compressed state for intraluminary catheter implantation. Once properly positioned adjacent the damaged treatment site in the body lumen, the stent is radially expanded so as to support and reinforce the body lumen. Radial expansion of the stent may be accomplished by inflation of a balloon attached to the catheter or the stent may be of the self-expanding variety which will radially expand once deployed and unconstrained. Tubular shaped structures, which have been used as intraluminary stents, have included helically wound coils which may have undulations or zig-zags therein, slotted stents, ring stents, braided stents and open mesh wire stents, to name a few. Super-elastic, metallic, and polymeric shape memory materials have been used to form stents. Additionally, fully bioabsorbable stents and stents coated with bioabsorbable materials such as bioelastomers have been made.

Although many stent delivery systems are well-known in the art, unlike metallic and most polymer self-expanding stents, stents made with bioabsorbable materials and bioelastomers may require constant hydration in order to retain their elastic properties. Also, tissue covered stents may require submersion in a liquid environment to maintain tissue hydration and health. Accordingly, there is a need for stent delivery systems that provide a liquid environment for the stent during transportation and delivery.

BRIEF SUMMARY

This disclosure provides design, material, and use alternatives for medical devices, including delivery systems.

A first example includes a stent delivery device. The device includes an inner member having a distal tip and a stent holding region proximal of the distal tip. The device also includes an outer tubular member slidingly disposed over the inner member. The outer tubular member has a distal end configured to engage the distal tip. The device also includes at least one first seal member disposed between the inner member and the outer tubular member proximal of the stent holding region, and at least one second seal member disposed between the distal tip and the outer tubular member. A combination of the first and second seal members defines a liquid-tight sealed chamber surrounding the stent holding region.

Alternatively or additionally to any of the above examples, the first seal member is disposed on an outer surface of the inner member.

Alternatively or additionally to any of the above examples, the first seal member is disposed on an inner surface of the outer tubular member.

Alternatively or additionally to any of the above examples, the second seal member is disposed on the distal tip.

Alternatively or additionally to any of the above examples, the second seal member is disposed on an inner surface of the distal end of the outer tubular member.

Alternatively or additionally to any of the above examples, the first seal member includes two or more separate seal members spaced apart around a circumference of the inner member.

Alternatively or additionally to any of the above examples, the first seal member is an O-ring disposed on an outer surface of the inner member.

Alternatively or additionally to any of the above examples, the second seal member includes two or more separate seal members spaced apart around a circumference of the distal tip.

Alternatively or additionally to any of the above examples, the second seal member includes a tapered region at the distal end of the outer tubular member, such that a diameter of the outer tubular member at the distal end is smaller than a diameter of the outer tubular member proximal of the distal end.

Alternatively or additionally to any of the above examples, the second seal member includes at least one circumferential protrusion disposed on an inner surface of the distal end of the outer tubular member.

Alternatively or additionally to any of the above examples, the distal tip includes a groove configured to receive the protrusion.

Alternatively or additionally to any of the above examples, the second seal member includes a tapered region at the distal end of the outer tubular member, such that a diameter of the outer tubular member at the distal end is smaller than a diameter of the outer tubular member proximal of the distal end, the second seal member further including at least one protrusion disposed on an inner surface of the tapered region at the distal end of the outer tubular member.

Alternatively or additionally to any of the above examples, the inner member includes a lumen with at least one port configured to deliver liquid to the chamber.

Alternatively or additionally to any of the above examples, the port includes a plurality of ports extending from the lumen into the chamber, the plurality of ports disposed along the stent holding region.

Alternatively or additionally to any of the above examples, the lumen extends from a proximal region of the inner member to the port, wherein the port is disposed proximal of the stent holding region.

Alternatively or additionally to any of the above examples, the device further includes a tubular member disposed adjacent the inner member, the tubular member extending from a proximal region to a distal end disposed within the chamber.

Alternatively or additionally to any of the above examples, the device further includes a stent stopper disposed around the stent holding region at a proximal end of the chamber, wherein the stent stopper includes an opening through which the tubular member extends.

Another example is a stent delivery device including an inner member having a distal tip, a stent holding region, and at least one first seal member disposed on an outer surface of the inner member proximal of the stent holding region. The device further includes an outer tubular member slidingly disposed over the inner member. The outer tubular member has a distal end configured to engage the distal tip. At least one of the distal tip and the distal end of the outer tubular member includes at least one second seal member, wherein a combination of the first and second seal members defines a liquid-tight sealed chamber surrounding the stent holding region.

Alternatively or additionally to any of the above examples, the first seal member includes two or more separate seal members spaced apart around a circumference of the inner member, wherein the second seal member includes at least one protrusion disposed on an inner surface of the distal end of the outer tubular member.

Another example is a method of loading a bioabsorable stent, retained in a liquid environment, into a delivery device. The method includes loading a bioabsorable stent onto a stent holding region of a stent delivery device. The stent delivery device includes an inner member having a distal tip, the stent holding region, a lumen, and at least one first seal member disposed on an outer surface of the inner member. The stent delivery device also includes an outer tubular member slidingly disposed over the inner member. The outer tubular member has a distal end configured to engage the distal tip. At least one of the distal tip and the outer tubular member includes at least one second seal member. A combination of the first and second seal members seals the outer tubular member to the inner member distal and proximal of the stent holding region. The method further includes sliding the outer tubular member distally over the bioabsorable stent until the distal end of the outer tubular member engages the distal tip, thereby forming a liquid-tight sealed chamber around the stent. The method further includes introducing liquid medium through the lumen in the inner member and into the liquid-tight sealed chamber to hydrate the stent.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE DRAWINGS

In the drawings, which are not necessarily drawn to scale, like numerals may describe similar components in different views. The drawings illustrate generally, by way of example, but not by way of limitation, various embodiments discussed in the present document.

FIGS. 3A-3H are close-up partial cross-sectional views of the distal region of the stent delivery device showing examples of details of the distal tip of the stent delivery device;

FIGS. 5A-5C are close-up partial cross-sectional views of the distal region of the stent delivery device showing examples of details of a fluid pathway into the hydration chamber of the stent delivery device.

Figure 1:
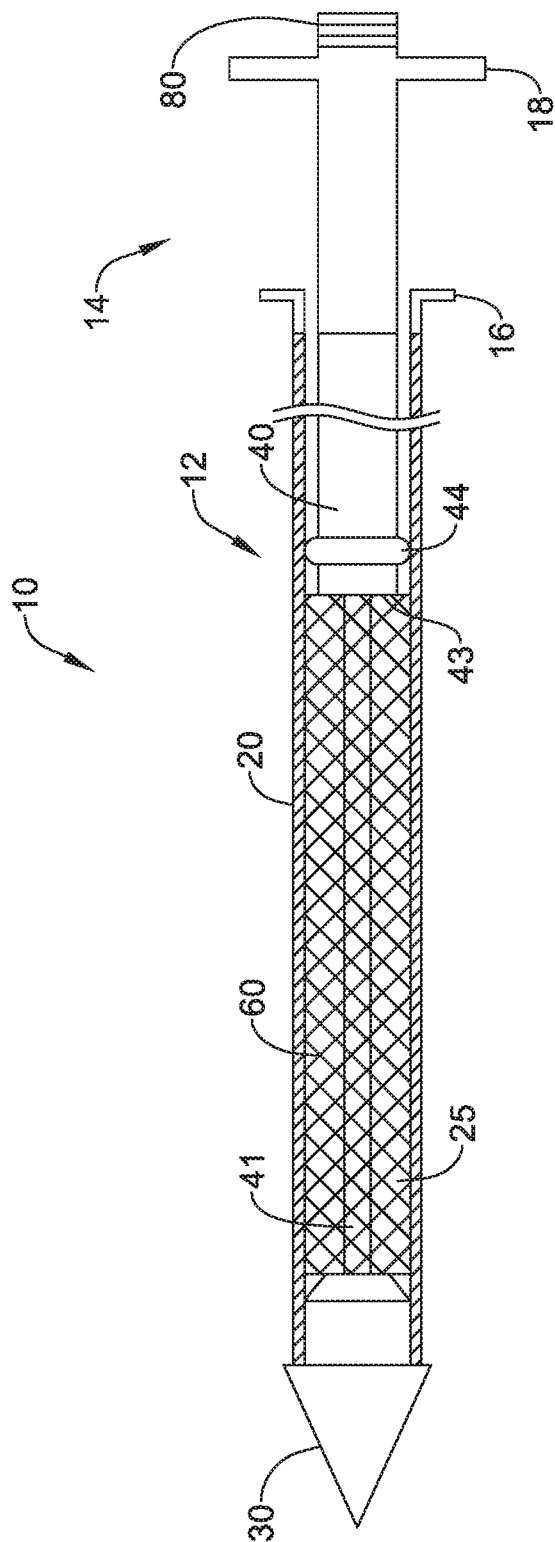
FIG. 1 is a partial cross-sectional view of a stent delivery device in accordance with an embodiment of the disclosure.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification. Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure. The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications may be disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

It is noted that references in the specification to "an embodiment", "an example", "some embodiments", "some examples", "another embodiment", "another example" etc., indicate that the embodiment or example described may include one or more particular features, structures, and/or characteristics. However, such recitations do not necessarily mean that all embodiments or examples include the particular features, structures, and/or characteristics. Additionally, when particular features, structures, and/or characteristics are described in connection with one embodiment or example, it should be understood that such features, structures, and/or characteristics may also be used connection with other embodiments and examples whether or not explicitly described unless clearly stated to the contrary.

References herein to the term "distal" and variants thereof refer to a direction away from an operator of the subject devices, while references to the term "proximal" and variants thereof refer to a direction towards the operator of the subject devices. Accordingly, when the terms "distal" and "proximal" are used herein in the context of an assembly device that is being deployed within a body, such as a human body, by an operator, the term "distal" refers to a location within or near the body that is further within the body than a location that is "proximal" or closer to the operator.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

FIG. 1 is a cross-sectional view of a stent loading and delivery system or device 10 according to the present invention. The device 10 is particularly well suited for the loading, transluminal delivery and intraluminal deployment of a radially self-expanding prosthesis in a liquid environment, such as a bioabsorbable stent and/or a stent-graft, which may be radially compressed and loaded into device 10, transluminally delivered to an intended intraluminal treatment site, then released from the system for radial self-expansion against surrounding tissue. While the present device can be applied to the delivery of many intraluminary devices, it is particularly suited for delivering the self-expanding stent 60 while the stent 60 is immersed in a liquid environment. The stent 60 is capable of being radially compressed and longitudinally extended for delivery into a bodily lumen. The degree of elongation depends upon the structure and materials of the stent 60 and may be quite varied. The diameter of the stent 60 also may become several times smaller as it is radially compressed. The stent 60 may be constructed to self-expand when unconstrained, and thus released from a radially compressed state to expand to a radially expanded state. Any stent that is capable of radial expansion may be used in accordance with the present device. For example, a radially distensible stent which does not substantially longitudinally elongate upon radial contraction is also useful. Various stent types and stent constructions may be employed in the device 10, and the device 10 may be constructed to accommodate stents of various sizes and configurations.

One example of the present device applies to a bioabsorbable stent 60. As used herein the term bioabsorbable and the related terms biodegradable and bioresorbable, refer to the property of being capable of being absorbed or resorbed into living tissue, or degrading when disposed in living tissue, such that the stent is cleared from the body, leaving no permanent implant. In some examples, a fully bioabsorbable stent is coated in a bioelastomer, and the resulting stent structure requires constant hydration in order to retain its elastic properties. Another example includes a tissue covered stent for prophylactic healing after esophageal resection or other injuries. Such a stent may require submersion in media to maintain tissue hydration and health. It is noted that in some instances, a only portion of stent 60 may be bioabsorbable, bioresorbable and/or biodegradable (e.g., a covering layer), while other portions of stent 60 may be biostable. However, in other instances, stent 60 may be fully bioabsorbable, bioresorbable and/or biodegradable.

Useful and nonlimiting examples of bioabsorbable or biodegradable polymeric materials from which a stent may be made include poly(L-lactide) (PLLA), poly(D,L-lactide) (PLA), poly(glycolide) (PGA), poly(L-lactide-co-D,L-lactide) (PLLAIPLA), poly(L-lactide-co-glycolide) (PLLAIPGA), poly(D,L-lactide-co-glycolide) (PLAIPGA), poly(glycolide-co-trimethylene carbonate) (PGAIPTMC), polydioxanone (PDS), Polycaprolactone (PCL), polyhydroxybutyrate (PHBT), poly(phosphazene) poly(D,L-lactide-co-caprolactone) PLAIPCL), poly(glycolide-co-caprolactone) (PGA/PCL), poly(phosphate ester) and the like. Further, the stent 60 may include materials made from or derived from natural sources, such as, but not limited to collagen, elastin, glycosaminoglycan, fibronectin and laminin, keratin, alginate, combinations thereof and the like.

Further, the stent 60 may be made from bioabsorbable polymeric materials which may also include radiopaque materials, such as metallic-based powders or ceramic-based powders, particulates or pastes which may be incorporated into the polymeric material. For example, the radiopaque material may be blended with the polymer composition from which the polymeric stent is formed, and subsequently fashioned into the stent as described herein. Alternatively, the radiopaque material may be applied to the surface of the stent. Various radiopaque materials and their salts and derivatives may be used including, without limitation, bismuth, barium and its salts such as barium sulfate, tantalum, tungsten, gold, platinum and titanium, to name a few. Additional useful radiopaque materials may be found in U.S. Pat. No. 6,626,936, which is herein incorporated by reference in its entirety. The stent 60 may be selectively made radiopaque at desired areas along the stent or may be fully radiopaque, depending on the desired end-product and application.

Also, the stent 60 may include coverings, films, coatings, and the like disposed over, under or throughout or embedding an expandable scaffold of the stent 60. For example, the stent 60 may include a covering, such as a bioabsorbable polymeric covering, disposed over the longitudinal length or a portion of the longitudinal length of an expandable tubular scaffolding of the stent 60. Further, the stent 60 may include a liner, such as a bioabsorbable polymeric liner, disposed within the longitudinal length or a portion of the longitudinal length of an expandable tubular scaffolding of the stent 60. Moreover, the stent 60 may include both a covering and a liner, such as a bioabsorbable polymeric covering and liner which include the same or different bioabsorbable polymeric materials, disposed over and within the longitudinal length or a portion of the longitudinal length of an expandable tubular scaffolding of the stent 60. The covering and/or the liner may be a unitary film or coating that embeds or partially embeds the expandable tubular scaffold of the stent 60. In some instances, the covering and/or liner may be applied to the tubular scaffold of the stent 60 in a dip coating or spray coating process. The bioabsorbable covering and/or the liner may be in the form of a tubular structure, for example composed of polymeric material and/or silicone. The covering and/or the liner may be transparent or translucent, desirably substantially or partially transparent. Furthermore, the bioabsorbable covering and/or the liner may be constructed of any suitable bioabsorbable materials as discussed above with regard to the stent 60.

In some examples, the stent 60 may be treated with a therapeutic agent or agents, such as, but not limited to, anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

As shown in FIG. 1, the stent 60 may have a straight or substantially straight longitudinal configuration. The present disclosure, however, is not so limited. For example, the stent 60 may have a varied diameter, such as a flaring or tapering, along a portion or portions of its longitudinal expanse. One non-limiting example of a varied diameter stent is a stent having a longitudinal body and a flared end at the first and/or second end of the stent (not shown). Flared ends may have a diameter greater than the diameter of the longitudinal body of the stent 60 between the flared ends. The stent 60, however, is not so limited, and for example flared ends, individually or in combination, may have a smaller diameter that the diameter of at least a portion of the longitudinal body of the stent 60. Further, the stent 60 may be repositionable, removable and/or reconstrainable, and/or may include multiple interconnected or non-interconnected stents.

As shown in FIG. 1, the device 10 may include an elongate catheter shaft 12 extending distally from a handle assembly 14. The elongate catheter shaft 12 may include an elongate, flexible inner member 40 with a distal tip 30, disposed and slidable within the lumen of an outer tubular member 20, interrelated as shown. The distal tip 30 is useful for navigating bodily lumens without causing trauma to the same. In some instances, the inner member 40 may be a tubular member defining a lumen extending therethrough. In some instances, the lumen of the inner member 40 may extend through the distal tip 30 for navigation of the device 10 over a guidewire, for example.

The proximal end of the outer tubular member 20 may be secured to a first, distal handle 16 of the handle assembly 14 and the inner member 40 may be secured to a second, proximal handle 18 of the handle assembly. The handle 16 may be actuated (e.g., longitudinally actuated) relative to the handle 18 in order to longitudinally actuate or move the outer tubular member 20 relative to the inner member 40.

Figure 5B:
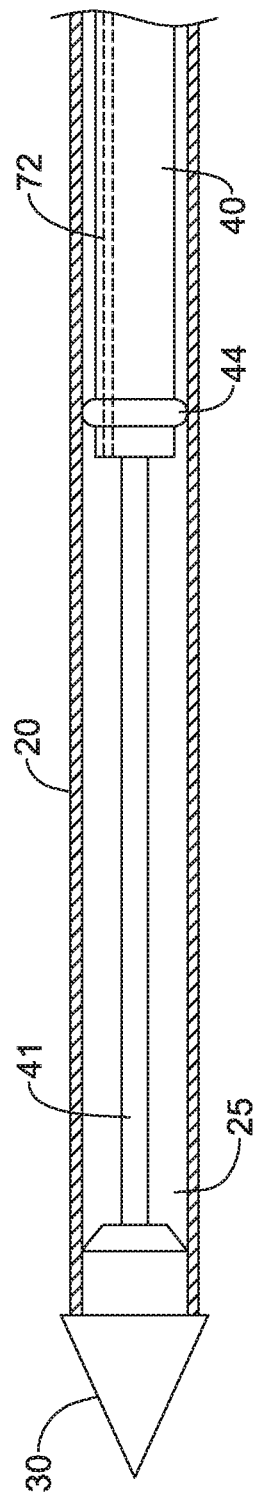
Figure 5C:
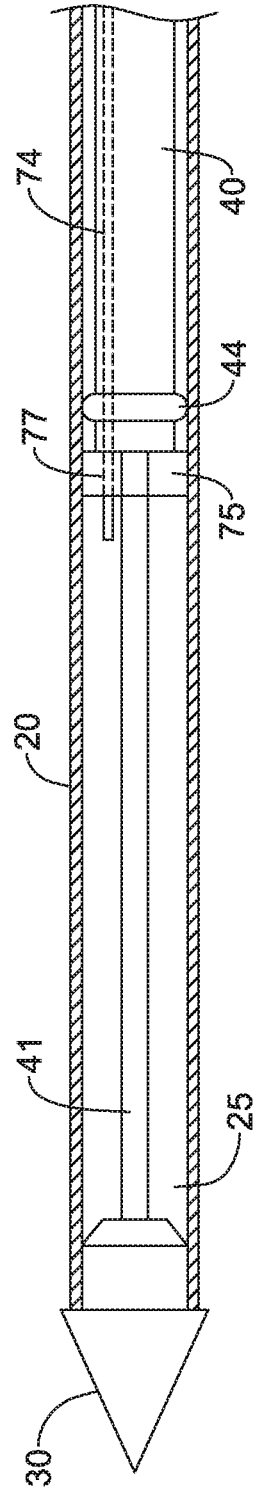

The inner member 40 may include a stent holding region 41 at a distal end region thereof around which the stent 60 may be positioned in a compressed state. The stent holding region 41 may have a diameter smaller than the diameter of the inner member 40 proximal of the stent holding region 41. A shoulder 43 between the narrower stent holding region 41 and the wider proximal portion of the inner member 40 may serve as a proximal stop preventing the stent 60 from moving proximally when the outer tubular member 20 is withdrawn proximally over the stent 60. In other examples, a stent stopper 75 may be provided, as shown in FIG. 5C. The outer tubular member 20 is sized to slide over, or otherwise be positioned over and surround the constrained stent 60, and thus constrain or radially compress the stent 60 in a radially constrained or compressed configuration, with the stent holding region 41 of the inner member 40 extending through the lumen of the stent 60. The outer tubular member handle 16, which may be disposed at and fixedly secured to the proximal end of the outer tubular member 20, may be used to advance and retract the outer tubular member 20 over the stent 60.

In order to provide a liquid environment for the stent 60, a sealable chamber 25 for holding the stent 60 may be formed between the inner surface of the outer tubular member 20 and the outer surface of the stent holding region 41 of the inner member 40 along the longitudinal extent of the stent 60, such as between the distal tip 30 and the shoulder 43 of the inner member 40. The sealable chamber 25 may be created by sealing members disposed on one or more of the distal tip 30, the inner member 40, and the outer tubular member 20. Water-tight seals may be created between the distal tip 30 and the distal end of the outer tubular member 20 distal of the distal end of the stent 60, and between the outer tubular member 20 and the inner member 40 proximal of the proximal end of the stent 60.

Features may be added to the outer surface of the inner member 40 and/or the inner surface of the outer tubular member 20 to create a seal between the inner member 40 and the outer tubular member 20 at the proximal end of the chamber 25. Furthermore features may be added to the outer surface of the distal tip 30 and/or the inner surface of the outer tubular member 20 to create a seal between the outer tubular member 20 and the distal tip 30 at the distal end of the chamber 25. The features may be discrete but circumferentially continuous around the inner member 40, the outer tubular member 20 and/or the distal tip 30 in one or more rows, depending on the desired (or necessary) strength of the seal. FIGS. 2A-4C illustrate various examples of features that may be provided on one or more of the distal tip 30, inner member 40, and outer tubular member 20 to provide a sealed chamber 25 in which the stent 60 resides. The stent 60 has been removed from FIGS. 2A-5C for clarity.

Figure 2A:
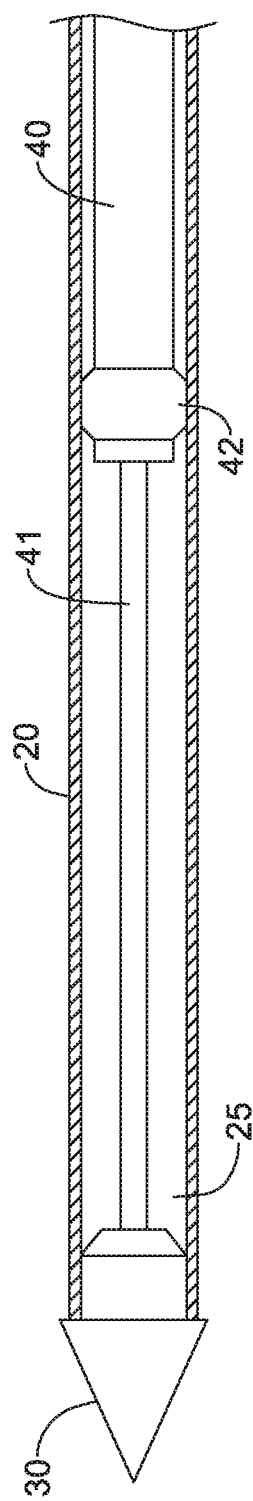
FIGS. 2A and 2B are close-up partial cross-sectional views of the distal region of the stent delivery device showing examples of details of the inner member of the stent delivery device.
Figure 2B:
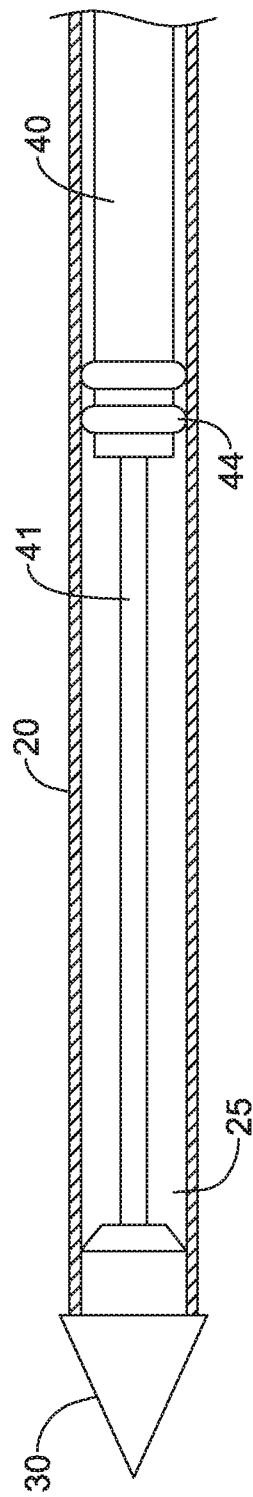

FIG. 2A illustrates a seal member 42 circumferentially surrounding the inner member. The seal member 42 is shown with angular surfaces. The seal member 42 may be secured to the inner member 40 and/or formed integrally with the inner member 40. In some examples, a plurality of seal members may be disposed circumferentially around the inner member 40 at spaced apart locations. FIG. 2B shows two continuous O-ring shaped seal members 44 that continuously surround the entire circumference of the inner member 40. The inner member 40 may have recessed grooves to accommodate part of the thickness of the seal member 44 when the seal member 44 is arranged in the recessed groove, or the seal member 44 may be added on top of the inner member 40 with adhesive, for example.

When the outer tubular member 20 is advanced distally over the inner member 40, the seal members 42, 44 engage the inner surface of the outer tubular member 20, forming a liquid-tight seal between the inner member 40 and the outer tubular member 20. In some examples, the seal member 42, 44 may be rigid, forming the seal based on a friction fit against the inner surface of the outer tubular member 20. In other examples, the seal members 42, 44 may be compressible, and may be compressed as the outer tubular member 20 is advanced distally over the seal members 42, 44.

Similar to the seal members 42, 44 shown on the inner member 40 in FIGS. 2A and 2B, seal members 50-57, shown in FIGS. 3A-3H, may be disposed on the proximal portion 31 of the distal tip 30 that engages the inner surface of the outer tubular member 20. The addition of these seal members 50-57 may decrease the space between the proximal portion 31 of the distal tip 30 and the outer tubular member 20, forming a liquid-tight seal at the distal end of the chamber 25 and retaining liquid within the chamber 25. When the outer tubular member 20 is advanced distally over the proximal portion 31 of the distal tip 30, one or more of the seal members 50-57 may engage the inner surface of the outer tubular member 20, forming a liquid-tight seal between the distal tip 30 and the outer tubular member 20. In some examples, the seal members 50-57 may be rigid, forming the seal based on a friction fit against the inner surface of the outer tubular member 20. In other examples, the seal members 50-57 may be compressible, and may be compressed as the outer tubular member 20 is advanced distally over the proximal portion 31 of the distal tip 30.

The seal members 50-57 form a releasable friction seal against the inner surface of the outer tubular member 20. When the stent 60 is to be released, the outer tubular member 20 may be withdrawn proximally from the distal tip 30, releasing the seal and opening the liquid-tight chamber 25.

Figure 3B:
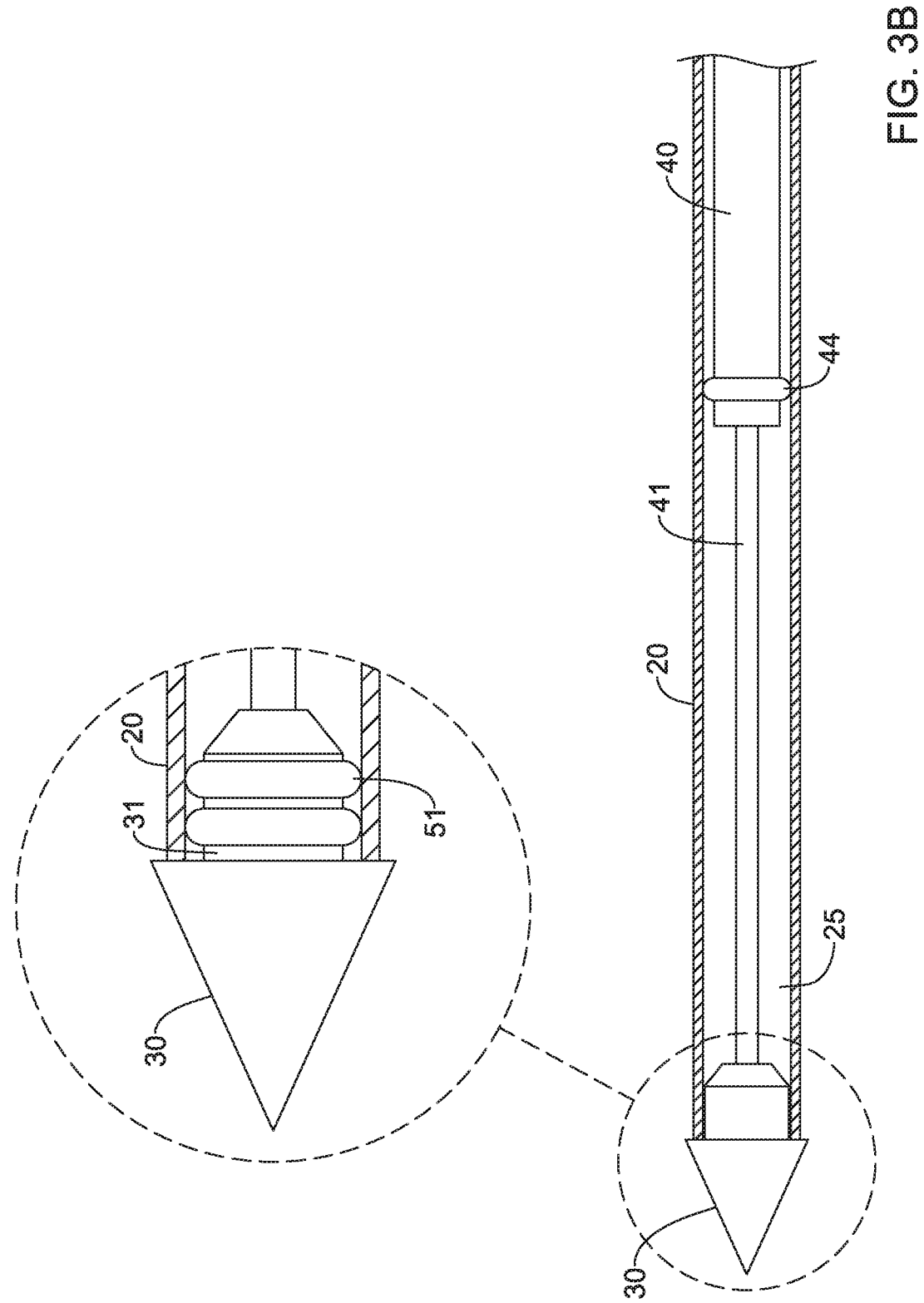
Figure 3C:
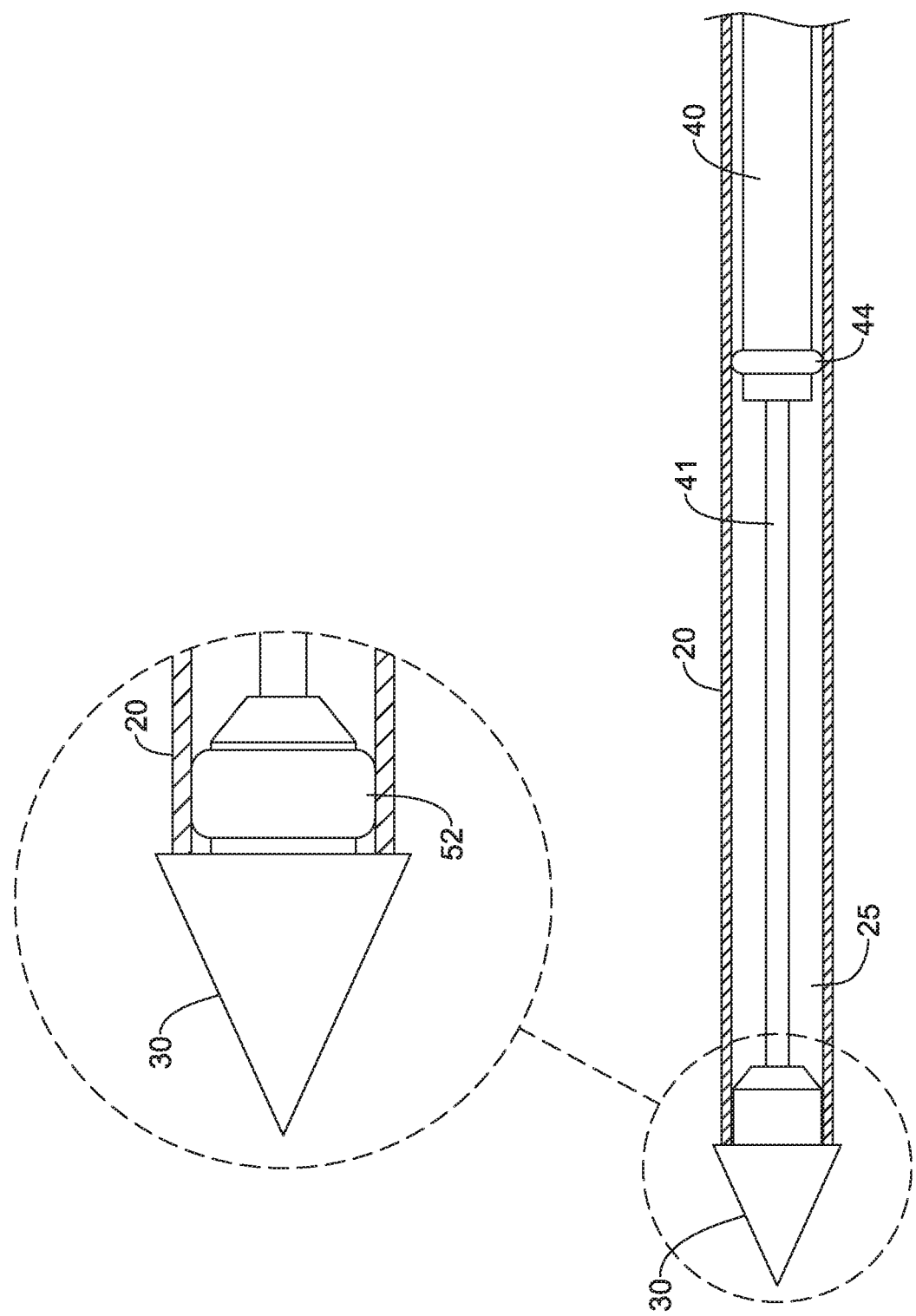
Figure 3E:
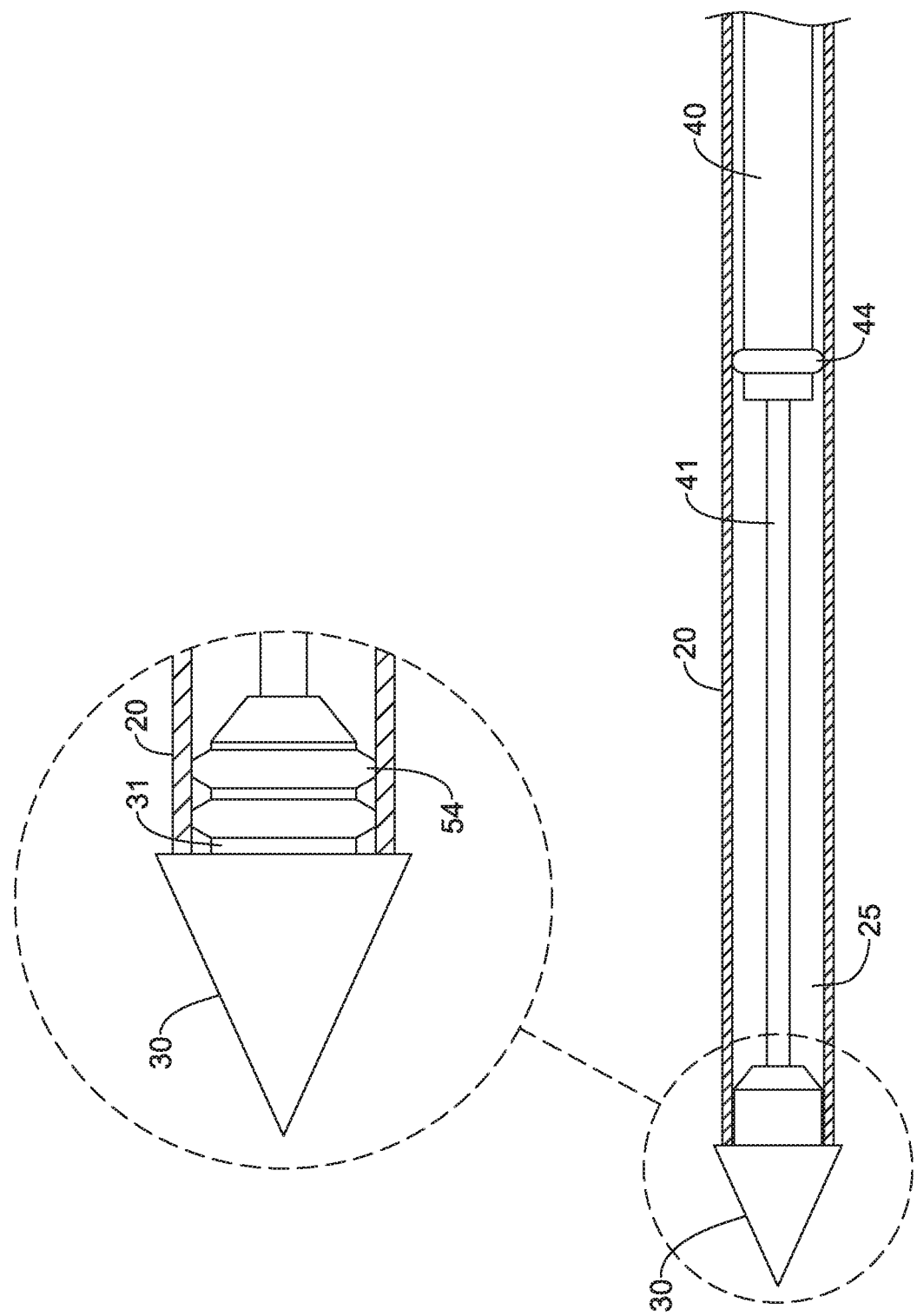
Figure 3F:
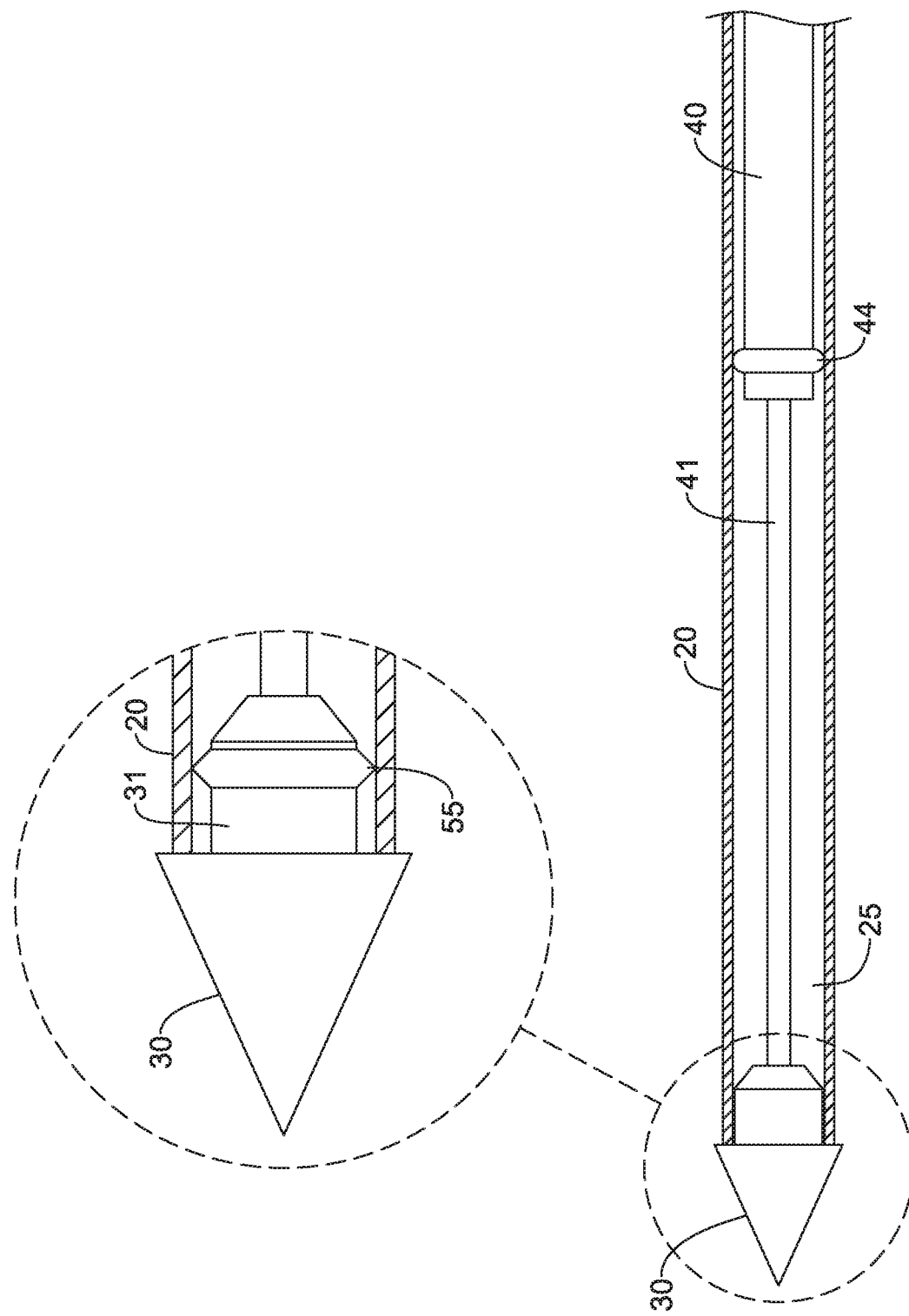
Figure 3G:
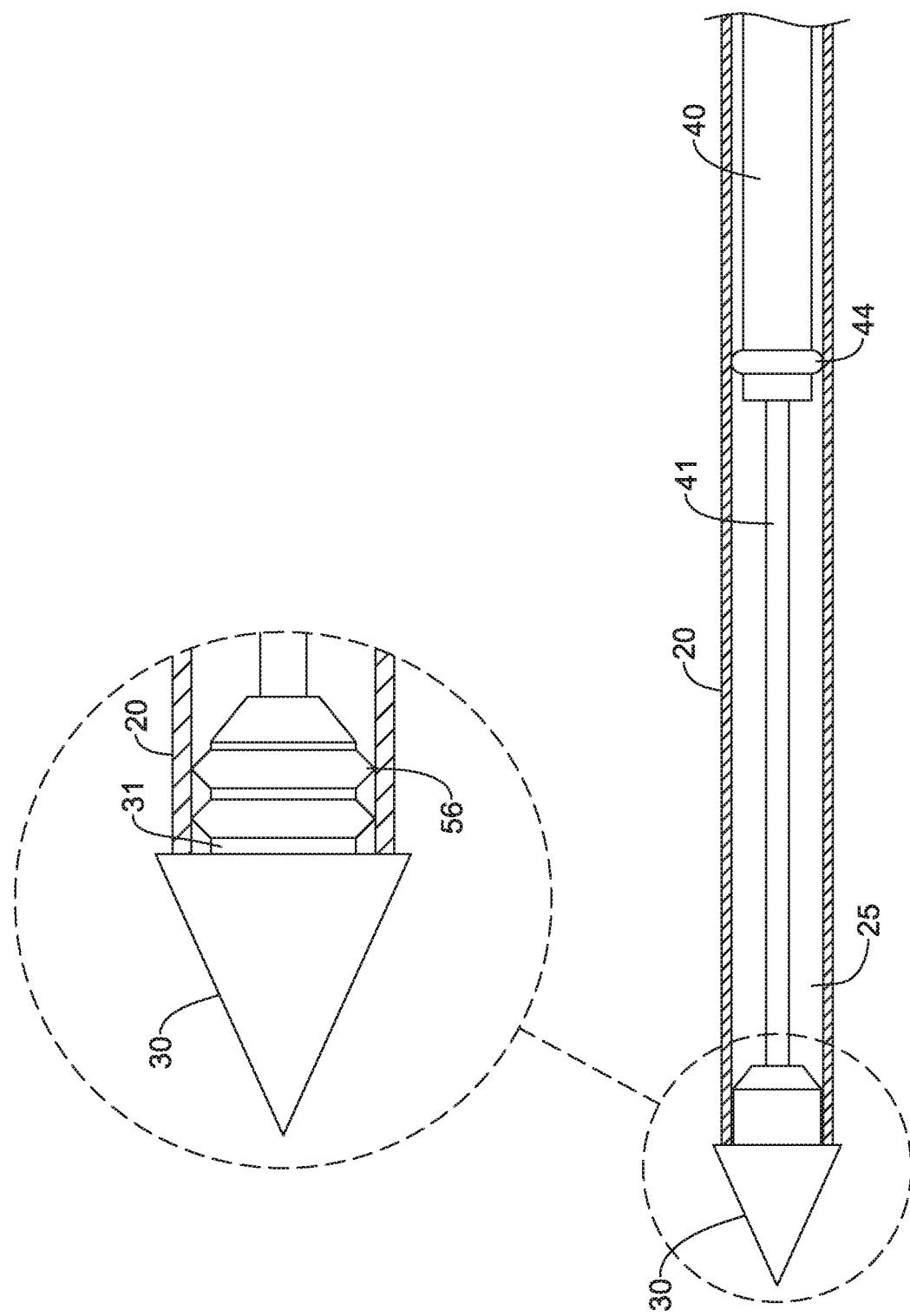

FIGS. 3A-3H illustrate various configurations and shapes of seal members 50-57. For example, seal member 50 shown in FIG. 3A has a rounded outer surface, and the pair of seal members 51 positioned adjacent each other shown in FIG. 3B also include a rounded outer surface. Seal member 52, shown in FIG. 3C, is elongated and has a flat top and rounded side surfaces. Seal member 53, shown in FIG. 3D, has a polygonal cross-sectional shape with a flat top, while FIG. 3E illustrates a pair of seal members 54 adjacent one another with a polygonal cross-sectional shape. The seal member 55, shown in FIG. 3F, has a triangular shape with a pointed tip configured to engage the inner surface of the outer tubular member 20. FIG. 3G illustrates a pair of seal members 56 adjacent one another having triangular cross-sectional shapes. The seal member 57, shown in FIG. 3H, is elongated with a pointed circumferential edge configured to engage the inner surface of the outer tubular member 20.

The seal members 50-57 may be added at any or all points around the circumference of the proximal portion 31 of the distal tip 30, depending on the desired seal. The mold used to make the distal tip 30 may be modified to include the seal members 50-57, such that the distal tip 30 and seal members 50-57 are made from the same flow of material. Alternatively, the seal members 50-57 may be added on after the distal tip 30 is molded using additive technology. Additionally to the seal member shapes shown in FIGS. 3A-3H, the O-ring shaped seal members 44 illustrated in FIG. 2B may also be used on the distal tip 30. The O-ring shaped seal members 44 may be molded as part of the distal tip 30, the O-ring shaped seal members 44 may be arranged in a circumferential groove in the proximal portion 31 of the distal tip 30, or the O-ring shaped seal members 44 may be added to the distal tip 30 with adhesive, for example. In further examples, any of the seal member shapes illustrated in FIGS. 3A-3H may be used on the inner member 40.

Any number of seal members 42, 44, 50-57 may be provided on the inner member 40 and/or on the proximal portion 31 of the distal tip 30. While FIGS. 2A, 2B and 3A-3H show a single shape and orientation for the seal members 42, 44, 50-57, it will be understood that a plurality of multiple different shapes of seal members may be present on the inner member 40 and/or on the proximal portion 31 of the distal tip 30. In some instances, the seal members 42, 44, 50-57 may be disposed on the inner member 40 adjacent the shoulder 43, and on a portion of or the entire proximal portion 31 of the distal tip 30. When multiple seal members 42, 44, 50-57 are present, they may extend over a distance of 1-20 mm of the inner member 40 and/or distal tip 30, for example.

Figure 4A:
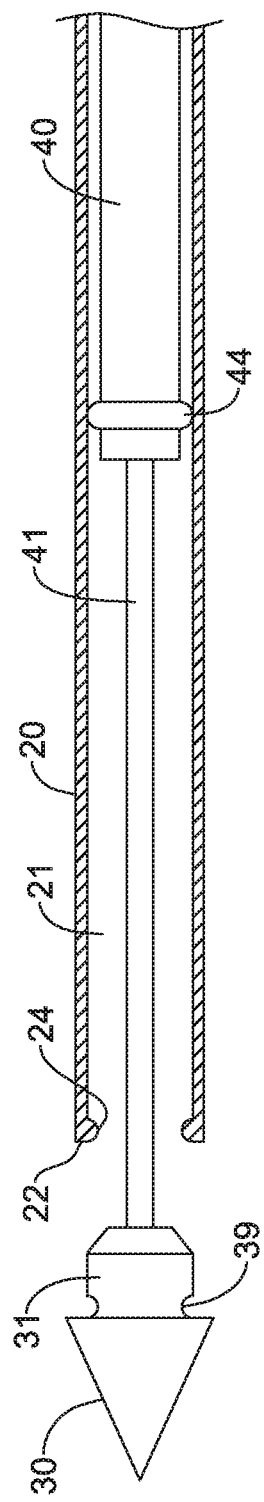
FIGS. 4A-4C are close-up partial cross-sectional views of the distal region of the stent delivery device showing examples of details of the distal end of the stent delivery device.
Figure 4B:
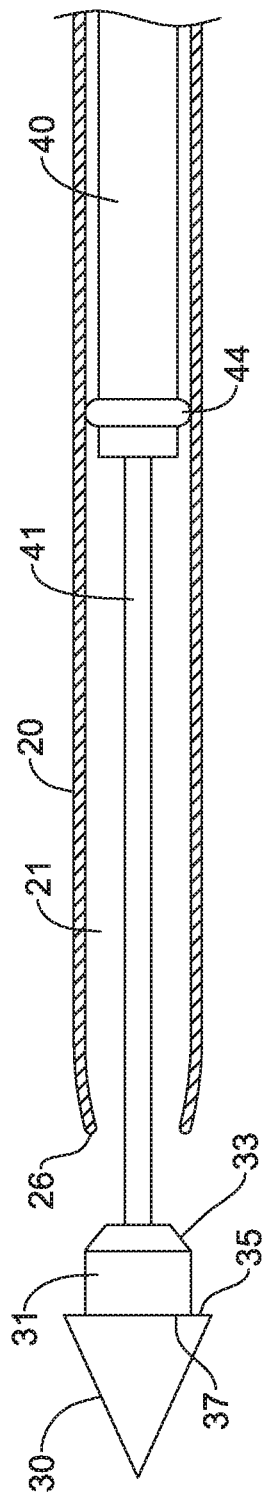
Figure 4C:
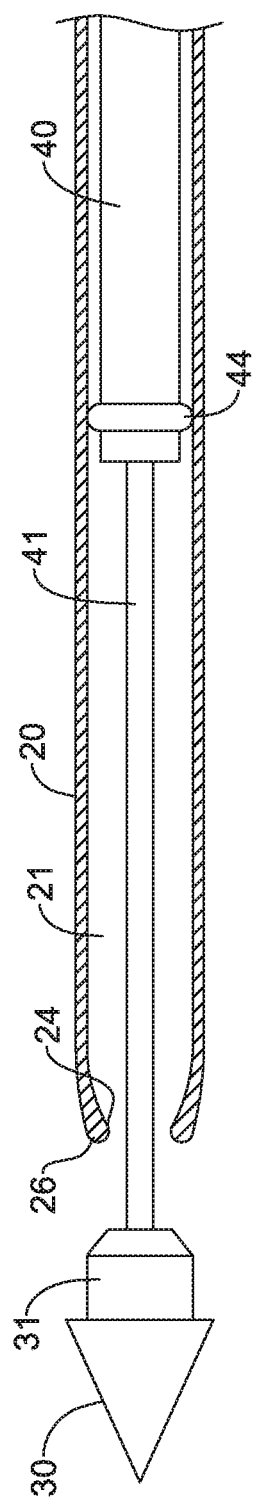

Additionally or alternatively, the shape and construction of the distal end 22 of the outer tubular member 20 may be altered to create a seal between the proximal portion 31 of the distal tip 30 and the outer tubular member 20, as shown in FIGS. 4A-4C. In FIG. 4A, the inner diameter of the outer tubular member 20 decreases at the distal end 22 due to addition of material forming a circumferential protrusion 24 extending radially inward toward the central longitudinal axis of the outer tubular member 20 into the lumen 21 of the outer tubular member 20 at the distal end 22. The protrusion 24 may extend around the entire inner circumference of the outer tubular member 20. The protrusion 24 may be made of the same or different material as the outer tubular member 20. If the protrusion 24 is made of the same material, extrusion properties could be altered to allow for thickening of the extrusion at the distal end 22 of the outer tubular member, whereas a different material may be added post extrusion, or during a different phase of the extrusion process, if desired. The protrusion 24 may be compressible or incompressible. The protrusion 24 may be added in a way that creates curvature, which may allow the protrusion 24 to travel smoothly over the beveled proximal end 33 of the proximal portion 31 of the distal tip 30 despite the decreased inner diameter of the distal end 22 of the outer tubular member 20.

In some examples, the outer tubular member 20 may have a taper 26 at the distal end 22 such that the inner diameter is decreased at the distal end 22 without adding a protrusion or thickening the material of the outer tubular member 20, as shown in FIG. 4B. In other examples, both the protrusion 24 and a taper 26 may be present at the distal end 22 of the outer tubular member, as shown in FIG. 4C. The beveled proximal end 33 of the distal tip 30 may aid in moving the tapered distal end 22 of the outer tubular member 20 over the proximal portion 31 of the distal tip 30. The distal end 22 of the outer tubular member 20 may be advanced distally over the angled proximal end 33 and proximal portion 31 of the distal tip 30 until the distal end 22 abuts the shoulder 35 defined by a distal portion 37 of the distal tip 30 that has a diameter larger than the proximal portion 31.

When the outer tubular member 20 is advanced distally over the inner member 40, the protrusion 24 engages the proximal portion 31 of the distal tip 30, forming a liquid-tight seal between the distal tip 30 and the outer tubular member 20. In some instances, the diameter of the opening into the lumen 21 of the outer tubular member 20 at the distal end of the outer tubular member 20 in a equilibrium state may be less than the outer diameter of the proximal portion 31 of the distal tip 30. In some examples, the protrusion 24 may be rigid, forming the seal based on a friction fit against the distal tip 30. In other examples, the protrusion 24 may be compressible, and may be compressed as the outer tubular member 20 is advanced distally over the distal tip.

In some examples, a notch or groove 39 may be cut circumferentially around the proximal portion 31 adjacent the shoulder 35 to accept the protrusion 24 and/or the taper 26 at the distal end 22 of the outer tubular member 20, creating a strong mechanical seal, as shown in FIG. 4A. In examples with a groove 39 on the proximal portion 31 of the distal tip 30, a compressible protrusion 24 may return to a non-compressed or equilibrium state when the protrusion 24 is positioned within the groove 39.

The protrusion 24 and/or taper 26 at the distal end 22 of the outer tubular member 20 may form a releasable friction seal against the proximal portion 31 of the distal tip 30. When the stent is to be released, the outer tubular member 20 may be withdrawn proximally from the distal tip 30, releasing the seal and opening the liquid-tight chamber 25 for deployment of the stent 60.

The chamber 25 may be filled with liquid via at least one port 70 into the chamber. In some instances, the inner member 40 may be a hollow tube having a lumen extending therein. The port(s) 70 may be made through the wall of the inner member 40 in the stent holding region 41 of the inner member 40 to provide fluid communication from the lumen of the inner member 40 into the chamber 25, as illustrated in FIG. 5A. As shown in FIG. 5A, the inner member 40 may include a plurality of ports 70 extending along at least a portion of the length of the stent holding region 41 in fluid communication with the lumen of the inner member 40. The port(s) 70 may be in fluid communication with a port 80 at the proximal end of the device 10 via the lumen of the inner member 40. In some instances, the proximal port 80 may be provided with the handle assembly 14, for example. A fluid source may be coupled to the port 80 to infuse fluid through the lumen of the inner member 40 into the chamber 25 through the port(s) 70.

In some examples, an additional channel may be created alongside the inner member 40. In the example shown in FIG. 5B, the additional channel is an additional lumen 72 added to the inner member extrusion. The lumen 72 may include a port opening into the chamber 25 at a proximal end of the stent holding region 41. The lumen 72 may be in fluid communication with the port 80 in the handle assembly 14. In the example shown in FIG. 5C, the additional channel is an additional tubular member 74 added parallel to the inner member 40. The tubular member 74 may be a separate element that is attached to the inner member 40 with adhesive. The tubular member 74 may be made of the same or a different material from the inner member 40. The tubular member 74 may include a port opening into the chamber 25 at a proximal end of the stent holding region 41. The tubular member 74 may be in fluid communication with the port 80 in the handle assembly 14. When a stent stopper 75 is present, an opening or notch 77 may be cut in the stent stopper 75 to allow passage of the tubular member 74 to pass through the stent stopper 75 and into the chamber 25. In another example, the tubular member 74 may be co-extruded with the inner member 40.

The injection port 80 may be disposed at the proximal handle assembly 14 to allow liquid to be pumped through or alongside the inner member 40 and into the chamber 25. In some examples, a pressure release could be added to the injection port 80 to ease liquid flow into the hydration chamber 25 and to reduce stagnant liquid in the access channel through the inner member 40. The seals between the distal tip 30 and the outer tubular member 20 and between the inner member 40 and the outer tubular member 20 may be sufficient to retain liquid in the chamber 25 from the time the stent 60 is loaded into the stent holding region 41 of the device 10, during shipping, and until the device 10 is inserted into a patient to a delivery site, at which time the seal may be broken as the stent is released from the device and deployed in a body lumen. In some instances, the injection port 80, the fluid delivery lumen (e.g., the lumen through the inner member 40, the additional lumen 72 or tubular member 74) and/or the port(s) 70 may include a one-way valve allowing fluid to enter the chamber 25 while preventing retrograde flow of fluid out of the chamber 25.

During stent deployment in which the outer tubular member 20 is withdrawn proximally relative to the stent 60, the seal between the outer tubular member 20 and the distal tip 30 is broken and liquid will release into the body lumen where the stent 60 is being deployed. A second catheter may be added down the delivery system presenting negative pressure to remove liquid before deployment, if desired. If the device 10 is used through a working channel of an endoscope, the suction capability of the endoscope could be used to collect the liquid as the stent 60 is deployed.

The structural features of the device discussed above may suitably be combined in any combination. In other words, all possible combinations of the features or structural elements of the present examples are contemplated, including all features and structural elements described in conjunction with the drawings.

Use of the device 10 is also contemplated by the present disclosure. Use of the device 10 may include a method for loading a self-expanding stent 60 into a delivery and deployment device 10 and delivering the stent 60 to a bodily lumen. The method may include radially contracting a stent 60 on a delivery device 10, the device 10 including an outer tubular member 20 having opposed proximal and distal ends, a longitudinal length and a lumen, an inner member 40 having opposed proximal and distal ends and a lumen, the inner member 40 slidably disposed within the outer tubular member 20, and a distal tip 30 disposed on the distal end of the inner member 40. A stent holding region 41 is provided on the inner member 40 between the distal tip 30 and the shoulder 43 of the inner member 40. A stent 60 is placed over the stent holding region 41 of the inner member 40 and within a hydration chamber 25 defined between proximal and distal seals. The distal seal provided between the distal tip 30 and the outer tubular member 20 and the proximal seal provided between the outer tubular member 20 and the inner member 40.

The outer tubular member 20 is advanced distally over the stent 60 until the distal end 22 engages the proximal portion 31 of the distal tip 30. One or more of the seal members 42, 44 on the inner member 40 may engage the inner surface of the outer tubular member 20 to form a liquid tight seal and define a proximal end of the chamber 25. One or more of the seal members 50-57 on the proximal portion 31 of the distal tip 30 may engage the inner surface of the outer tubular member 20 to form a liquid tight seal and define a distal end of the chamber 25. Alternatively, or in addition, the protrusion 24 and/or the taper 26 at the distal end 22 of the outer tubular member 20 may engage the proximal portion 31 of the distal tip 30 to form the liquid tight seal and define the distal end of the chamber 25. Once the outer tubular member 20 is advanced distally and engages the distal tip 30, the chamber 25 is sealed, as shown in FIG. 1. A liquid medium may then be inserted into the chamber 25, via one or more of the ports 70, additional lumen 72, or tubular member 74. The inner member 40 may have a lumen extending to a proximal end of the device 10, with an outlet port for delivering liquid through the inner member 40. In some instances, the injection port 80, the fluid delivery lumen (e.g., the lumen through the inner member 40, the additional lumen 72 or tubular member 74) and/or the port(s) 70 may include a one-way valve allowing fluid to enter the chamber 25 while preventing retrograde flow of fluid out of the chamber 25. The stent 60 may be packaged in this configuration, with the stent 60 secured within the liquid-filled chamber 25. Once the stent 60 has been delivered to a desired location within a patient's body, the method may further include axially moving or sliding the outer tubular member 20 proximally, breaking the seals and releasing the liquid within the chamber 25 and releasing the stent 60 for deployment in a body lumen of the patient.

The materials that can be used for the various components of the delivery device 10 and the various tubular members disclosed herein may include those commonly associated with medical devices. For simplicity purposes, the following discussion makes reference to outer tubular member 20 and inner member 40 and other components of device 10. However, this is not intended to limit the devices and methods described herein, as the discussion may be applied to other similar devices and/or components of devices or devices disclosed herein.

The outer tubular member 20 and inner member 40 may be formed of a body compatible material. Desirably, the biocompatible material is a biocompatible polymer. Examples of suitable biocompatible polymers include, but are not limited to, polyolefins such as polyethylene (PE), high density polyethylene (HDPE) and polypropylene (PP), polyolefin copolymers and terpolymers, polytetrafluoroethylene (PTFE), polyethylene terephthalate (PET), polyesters, polyamides, polyurethanes, polyurethaneureas, polypropylene and, polycarbonates, polyvinyl acetate, thermoplastic elastomers including polyether-polyester block copolymers and polyamide/polyether/polyesters elastomers, polyvinyl chloride, polystyrene, polyacrylate, polymethacrylate, polyacrylonitrile, polyacrylamide, silicone resins, combinations and copolymers thereof, and the like. Desirably, the biocompatible polymers include polypropylene (PP), polytetrafluoroethylene (PTFE), polyethylene terephthalate (PET), high density polyethylene (HDPE), combinations and copolymers thereof, and the like. The outer tubular member 20 and the inner member 40 may be made of the same material or they may be made of different materials.

The outer tubular member 20 and inner member 40 may also have a surface treatment and/or coating on their inner surface, outer surface or portions thereof. A coating need not be applied to both the outer tubular member 20 and the inner member 40, and individual members may be coated, uncoated, partially coated, and the like. Useful coating materials include any suitable biocompatible coating. Non-limiting examples of suitable coatings include polytetrafluoroethylene, silicone, hydrophilic materials, hydrogels, and the like. Useful hydrophilic coating materials include, but are not limited to, alkylene glycols, alkoxy polyalkylene glycols such as methoxypolyethylene oxide, polyoxyalkylene glycols such as polyethylene oxide, polyethylene oxide/polypropylene oxide copolymers, polyalkylene oxide-modified polydimethylsiloxanes, polyphosphazenes, poly(2-ethyl-2-oxazoline), homopolymers and copolymers of (meth) acrylic acid, poly(acrylic acid), copolymers of maleic anhydride including copolymers of methylvinyl ether and maleic acid, pyrrolidones including poly(vinylpyrrolidone) homopolymers and copolymers of vinyl pyrrolidone, poly (vinylsulfonic acid), acryl amides including poly(N-alkylacrylamide), poly(vinyl alcohol), poly(ethyleneimine), polyamides, poly(carboxylic acids), methyl cellulose, carboxymethylcellulose, hydroxypropyl cellulose, polyvinylsulfonic acid, water soluble nylons, heparin, dextran, modified dextran, hydroxylated chitin, chondroitin sulphate, lecithin, hyaluranon, combinations and copolymers thereof, and the like. Non-limiting examples of suitable hydrogel coatings include polyethylene oxide and its copolymers, polyvinylpyrrolidone and its derivatives; hydroxyethylacrylates or hydroxyethyl(meth)acrylates; polyacrylic acids; polyacrylamides; polyethylene maleic anhydride, combinations and copolymers thereof, and the like. Additional details of suitable coating materials and methods of coating medical devices with the same may be found in U.S. Pat. Nos. 6,447,835 and 6,890,348, the contents of which are incorporated herein by reference. Such coatings and/or surface treatment is desirably disposed on the inside or a portion thereof of the outer tubular member 20 to aid, if desired, in loading and/or deploying of the stent 60.

Additionally, the various components of the devices/systems disclosed herein may include a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 320LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRIL- AMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In at least some embodiments, portions or all of the delivery device 10 and/or other components of delivery system may be doped with, made of, or otherwise include a radiopaque material. Radiopaque materials are understood to be materials capable of producing a relatively bright image on a fluoroscopy screen or another imaging technique during a medical procedure. This relatively bright image aids the user of the delivery device 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the delivery device 10 to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A stent delivery device comprising:
    an inner member having a distal tip and a stent holding region proximal of the distal tip,
    an outer tubular member slidingly disposed over the inner member, the outer tubular member having a distal end configured to engage the distal tip while radially surrounding an entire length of the stent holding region, wherein when the distal end engages the distal tip, the outer member is configured to radially compress a stent disposed between the inner member and outer member along the stent holding region;
    at least one first seal member disposed between the inner member and the outer tubular member proximal of the stent holding region; and
    at least one second seal member disposed between the distal tip and the outer tubular member;
    wherein a combination of the first and second seal members defines a liquid-tight sealed chamber located radially between an outer surface of the stent holding region of the inner member and an inner surface of the outer tubular member.

2. The stent delivery device of claim 1, wherein the first seal member is disposed on an outer surface of the inner member.

3. The stent delivery device of claim 2, wherein the second seal member is disposed on an inner surface of the distal end of the outer tubular member.

4. The stent delivery device of claim 1, wherein the second seal member is disposed on an inner surface of the distal end of the outer tubular member.

5. The stent delivery device of claim 1, wherein the second seal member includes at least one circumferential protrusion disposed on an inner surface of the distal end of the outer tubular member.

6. The stent delivery device of claim 5, wherein the distal tip includes a groove configured to receive the protrusion.

7. The stent delivery device of claim 1, wherein the inner member includes a lumen with at least one port configured to deliver liquid to the chamber.

8. The stent delivery device of claim 7, wherein the port includes a plurality of ports extending from the lumen into the chamber, the plurality of ports disposed along the stent holding region.

9. The stent delivery device of claim 7, wherein the lumen extends from a proximal region of the inner member to the plurality of ports.

10. A stent delivery device comprising;
    an inner member having a distal tip, a stent holding region, and at least one first seal member disposed on an outer surface of the inner member proximal of the stent holding region; and
    an outer tubular member surrounding the stent holding region of the inner member while a distal end of the outer tubular member engages the distal tip, the outer tubular member longitudinally slideable relative to the inner member;
    wherein at least one of the distal tip and the distal end of the outer tubular member includes at least one second seal member, wherein a combination of the first and second seal members defines a liquid-tight sealed chamber located radially between an outer surface of the stent holding region of the inner member and an inner surface of the outer tubular member.

11. The stent delivery device of claim 10, wherein the second seal member includes at least one circumferential protrusion disposed on the inner surface of the outer tubular member.

12. The stent delivery device of claim 11, wherein the distal tip includes a groove configured to receive the protrusion.

13. The stent delivery device of claim 10, wherein the inner member includes a lumen with at least one port configured to deliver liquid to the chamber.

14. The stent delivery device of claim 13, wherein the port includes a plurality of ports extending from the lumen into the chamber, the plurality of ports disposed along the stent holding region.

15. A stent delivery assembly comprising:
    an outer tubular member having a lumen extending therethrough;
    an inner member having a distal tip and a stent holding region proximal of the distal tip, the inner member slidingly disposed through the lumen of the outer tubular member with the outer tubular member surrounding the stent holding region while a distal end of the outer tubular member engages the distal tip;
    a first seal member disposed between the inner member and the outer tubular member proximal of the stent holding region; and
    a second seal member disposed between the inner member and the outer tubular member distal of the stent holding region;
    wherein a combination of the first and second seal members defines a liquid-tight sealed chamber located radially between an outer surface of the stent holding region of the inner member and an inner surface of the outer tubular member; and a stent disposed within the liquid-tight sealed chamber radially between the inner member and the outer tubular member, the stent positioned between the first seal member and the second seal member along the stent holding region.

16. The stent delivery assembly of claim 15, wherein the inner member includes a lumen with at least one port configured to deliver liquid to the liquid-tight sealed chamber.

17. The stent delivery assembly of claim 15, wherein the inner member includes a lumen with a plurality of ports disposed along the stent holding region, the plurality of ports in fluid communication with the liquid-tight sealed chamber.

18. The stent delivery assembly of claim 15, wherein the second seal member includes at least one circumferential protrusion disposed on an inner surface of the outer tubular member.

19. The stent delivery assembly of claim 18, wherein the distal tip includes a groove receiving the protrusion.

\* \* \* \* \*